United States Patent [19]

Marfurt et al.

[11] 4,102,368

[45] Jul. 25, 1978

[54] DEVICE FOR SAMPLING FLUID

[75] Inventors: Hans Rudolf Marfurt; August Zürrer, both of Marly; Felix Gärtner, Rheinfelden, all of Switzerland

[73] Assignee: Ciba-Geigy AG, Basel, Switzerland

[21] Appl. No.: 775,926

[22] Filed: Mar. 9, 1977

[30] Foreign Application Priority Data

Mar. 16, 1976 [CH] Switzerland .................. 3265/76

[51] Int. Cl.² ............................................. B65B 3/26
[52] U.S. Cl. .................. 141/250; 23/252 R; 215/6; 220/20
[58] Field of Search ............. 23/293, 252 R, 253 R; 220/20; 215/1 R, 6; 141/129–191, 250–284

[56] References Cited
U.S. PATENT DOCUMENTS 3,684,452  8/1972  Bessman .......................... 141/130

Primary Examiner—Houston S. Bell, Jr.
Attorney, Agent, or Firm—Wenderoth, Lind & Ponack

[57] ABSTRACT

A device for sampling fluid is provided which comprises a plurality of sample vessels uniformly spaced apart in a circle and means for the alternate feeding of fluid into the individual sample vessels. A buffer vessel whose volume is at least three to five times greater than that of each individual sample vessel is connected upstream in series to the sample vessels. The sample vessels are U-shaped and have two substantially upright tubular arms which are joined together at their bottom ends. One arm is smaller in diameter and ends below the opening of the other arm or has a mouth or opening below the opening of the other arm. The means for feeding the fluid enter the thicker and higher arm of the sample vessels and are so built as to be able to empty the entire contents of the buffer vessel in the course of at most one to two minutes into the sample vessel.

12 Claims, 1 Drawing Figure

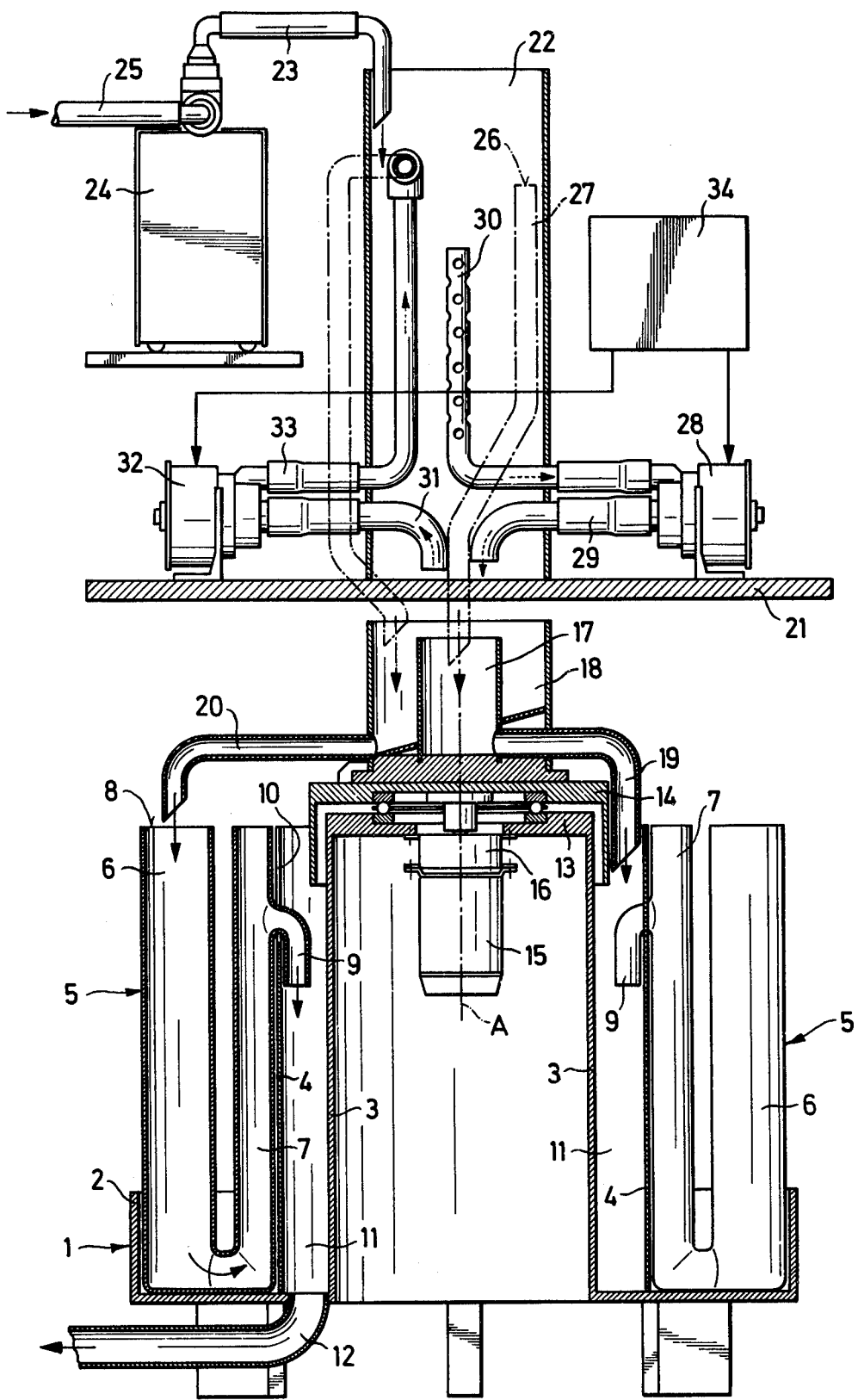

DEVICE FOR SAMPLING FLUID

BACKGROUND OF THE INVENTION

The invention relates to a device for sampling fluid comprising a plurality of sample vessels and means for the alternate feeding of fluid into the individual sample vessels.

In many fields of technology, in particular also that concerned with the prevention of water pollution, it is customary to take samples from fluids which are subjected to changes, for example from sewers and sewer conduits, preferably automatically at regular intervals of time. With the aid of these samples it is possible to obtain a precise picture of the state, or any changes in the state, of the fluid being analysed as well as of the chronological course of these changes. In many cases, however, in particular also in water pollution control, it is often not necessary to analyse all the samples of fluid constantly. Rather it is sufficient from time to time, or if special circumstances make it appear expedient, to make random tests. If a change in the state of the fluid is observed when making such a random test, and this change gives rise to further investigations, then the samples which have been taken during a specific period of time before this random test, for example over the previous 24 hours, are also analysed. In practice, this means that, at any time, the samples taken over a specific period of time before this time must always be available for analysis. Earlier samples, however, need not be kept.

A number of automatic devices for taking samples of fluid are already known. One of the most useful of these devices consists of a set of 24 sample vessels and a filling apparatus which charges the individual glass vessels at regular intervals of one hour per cycle. However, one of the most intrinsic disadvantages of this known device is that its sample vessels have to be emptied and rinsed each time within the duration of the cycle if it is to be avoided that, when the vessels are recharged, the new samples do not become mixed with the old ones or the residues thereof still present in them, so that the result of the analysis is falsified. This emptying and rinsing of the sample vessels requires either a constant supervision and maintenance of the the device or else, if the procedure is automatic, the provision of relatively complicated mechanical means.

SUMMARY OF THE INVENTION

The task of the invention is accordingly to provide a sampling device by means of which the periodic emptying and rinsing of the sample vessels is dispensed with or else is effected automatically with a minimum of technical resources. According to the invention, this task is accomplished by connecting upstream in series to the sample vessels a common buffer vessel whose volume is at least three to five times greater than that of each individual sample vessel, providing the sample vessels with two substantially upright tubular arms which are joined together at their bottom ends and one of which ends below the rim of the opening of the other or has an outlet below such rim, and by the means for feeding the fluid emptying into the latter arm of the sample vessel. The effect of a relatively large buffer vessel being connected upstream in series to the sample vessels, as well as of the special form of the sample vessels, is that, when a sample vessel is freshly charged, the old sample present therein is expelled virtually free of residue from the vessel and therefore an emptying and rinsing procedure is no longer necessary.

BRIEF DESCRIPTION OF THE DRAWING

The device of the present invention is described in greater detail hereinafter with reference to the drawing. The single FIGURE of the drawing shows a vertical section through a sampling device of the present invention in a somewhat diagrammatic view.

DETAILED DESCRIPTION OF THE INVENTION

Twenty-four sample vessels 5 are arranged uniformly spaced apart on a circular support 1 with a lower outside wall 2 and a higher inside wall 3 as well as a higher intermediate wall 4, in the annular space bounded by the outside wall and the intermediate wall. Each sample vessel 5 consists of two tubular arms of equal length 6 and 7 which are jointed together at their bottom ends to form a U-tube. The arm 7, which is situated radially further within in respect of the radius of the support, has a narrower diameter and is provided with a downwardly bent side mouth piece 9 which forms an outlet opening or an overflow below the level of the rim of the inlet opening 8 of the other radially external arm 6. The mouth pieces 9 of the sample vessels 5 project through apertures 10 which are provided in the intermediate wall 4 and uniformly spaced apart, so that fluid issuing therefrom is able to pass into the collecting duct 11 and from there to run off through a flow pipe 12. The mouth pieces 9 also serve at the same time as mountings for the sample vessels 5. It will be understood that, instead of the mouth pieces 9, the arms 7 of the sample vessels could also have simple outlets or the arm 7 could be shorter than the other arm 6. In that event, other means would naturally have to be provided for the mounting of the sample vessels. As will be seen later, the essential thing is that fluid can issue from this arm 7 below the level of the rim of the opening of the other arm.

The upper edge of the inside wall 3 carries a cover plate 13 on which a rotary plate 14 is pivoted. A synchronous motor 15 which drives the rotary plate 14 via a mechanism 16 with a rotating speed of one revolution per twenty-four hours about the axis A is mounted on the underside of the cover plate 13. Two coaxial beakers 17 and 18, which are open at the top, are mounted on the rotary plate 14. The inside beaker 17 is connected to a pipe 19 which projects into the space between the inside wall 3 and the intermediate wall 4, so that fluid which is present in the beaker 17 can run off through the pipe 19 into the collecting duct 11. The external beaker 18 is also connected to a downwardly bent pipe. This outlet pipe 20 extends to just above the opening 8 of the radially external arms 6 of the sample vessels 5 and in the course of its circular path passes over the mouths of the individual sample vessels at regular intervals of one hour. While this outlet pipe 20 passes over a sample vessel 5, fluid present in the beaker 18 thus passes through the outlet pipe 20 into the respective sample vessel.

Positioned above the two coaxial beakers 17 and 18, and mounted on an intermediate support 21, is an open buffer vessel 22 into which runs the delivery pipe 23 of a feed pump 24 whose suction pipe 25 is connected to the receptacle (not shown) of the fluid to be analysed. The feed pump 24 fills the buffer vessel 22 in the course of approx. one hour up to a level of the upper lip 26 of an overflow pipe 27. The overflow pipe runs through the intermediate support 21 and into the inner beaker 17 on the rotary plate 14.

A circulation pump 28 with a delivery pipe 29 which enters the buffer vessel near the bottom and a suction pipe 30 having a plurality of apertures, are provided for homogenising the contents of the buffer vessel.

A further suction pipe 31, which also enters the buffer vessel near the bottom, is connected to a drawing-off pump 32. The delivery pipe 33 of this drawing-off pump forms a siphon which projects just above the upper lip of the overflow pipe 27 and enters the external beaker 18 on the rotary plate 14. The capacity of the drawing-off pump 32 and the diameter of its suction and delivery pipes as well as of the outlet pipe 20 of the beaker 18 are so dimensioned that the entire contents of the buffer vessel 22, which are determined by the level of the lip 26 of the overflow pipe 27 and which must be at least approx. three to five times greater than that of a sample vessel, can be emptied in approx. one to two minutes.

Finally, a timing means 34 is provided for controlling the drawing-off pump 32 and the circulation pump 28.

Starting from the empty buffer vessel 22, the operation proceeds more or less as follows: The feed pump 24 feeds the fluid to be analysed continuously to the buffer vessel. During this time, the outlet pipe 20 slowly moves from the just filled sample vessel to the next one. After approx. 45 minutes, the timing means 34 activates the circulation pump 28, which then effects a thorough mixing and homogenisation of the contents of the buffer vessel. After 59 minutes, the outlet pipe 20 has reached the next sample vessel. The drawing-off pump 32 is then activated by the timing means 34 and the entire contents of the buffer vessel are emptied via the delivery pipe 33, the external beaker 18 and the outlet pipe 20 into the radially external thicker arm 6 of the sample vessel 5. The circulation pump is simultaneously deactivated. The emptying procedure lasts approximately one minute, which is substantially less than the time required for the outlet pipe 20 to pass over the opening 8 of the arm 6 of the sample vessel. Thereafter the drawing-off pump is deactivated and a new cycle commences.

Any old sample present in the sample vessel 5 is expelled through the mouth piece 9 into the collecting channel. This expulsion is almost complete on account of the special shape of the sample vessel, of the approximately three to five times greater volume of the buffer vessel, and of the relatively rapid drawing-off procedure. Practical experiments using a 1N solution of sodium chloride have resulted in degrees of expulsion of 99.84%. The device of the present invention therefore makes it possible to dispense with emptying and rinsing out sample vessels with contents which are not intended for analysis. Consequently, it requires neither supervision and maintenance nor additional complicated mechanical means for emptying and rinsing.

We claim:

1. A fluid sampling device comprising:
   a vessel support;
   a plurality of sample vessels supported on said vessel support, each said sample vessel including first and second substantially upright tubular arms, said first and second arms being joined at bottom ends thereof, said first arm having an upper end with an inlet opening therein, said second arm having an outlet opening therein, and said outlet opening being at a level below said inlet opening; and
   means for sequentially feeding a fluid to be sampled to each of said sample vessels, said feeding means comprising a single buffer vessel adapted to receive therein fluid to be sampled, said buffer vessel having a volume at least three to five times as large as the volume of each said sample vessel, and means for sequentially supplying fluid from said buffer vessel to said first arms of said sample vessels.

2. A device as claimed in claim 1, wherein said feeding means further comprises means for emptying all fluid within said buffer vessel into one of said sample vessles in a time period of no more than one to two minutes.

3. A device as claimed in claim 1, further comprising means for mixing fluid within said buffer vessel.

4. A device as claimed in claim 3, wherein said feeding means further comprises a pump for sequentially emptying fluid from said buffer vessel to said sample vessels.

5. A device as claimed in claim 4, further comprising timing means for synchronously activating and deactivating said mixing means and said pump.

6. A device as claimed in claim 1, wherein said feeding means further comprises a pump for sequentially emptying fluid from said buffer vessel to said sample vessels.

7. A device as claimed in claim 1, wherein said sample vessels are uniformly spaced apart in a circle about an axis, said supplying means comprises a single outlet pipe connected to said buffer vessel, said outlet pipe is mounted for rotation about said axis, and said outlet pipe extends radially from said axis by a distance to align with said first arms of said sample vessels.

8. A device as claimed in claim 7, wherein said sample vessels are mounted on said vessel support with said first arms positioned radially outwardly of said second arms.

9. A device as claimed in claim 7, wherein twenty-four sample vessels are provided, and further comprising means for rotating said outlet pipe about said axis at a speed of one revolution per twenty-four hours.

10. A device as claimed in claim 1, wherein said second arm of each said sample vessel has therein a downwardly bent mouthpiece forming an overflow, said outlet opening being in said mouthpiece.

11. A device as claimed in claim 10, wherein said vessel support includes a cylindrical wall, said first and second arms of each said sample vessel are aligned in a plane extending radially of said wall, and said mouthpiece of each said sample vessel extends through an opening in said wall, said sample vessels thereby being supported by engagement of said mouthpieces with said wall.

12. A device as claimed in claim 1, wherein the horizontal cross-sectional area of said first arm of each said sample vessel is greater than that of said second arm.

* * * * *